United States Patent [19]
Guglielmetti et al.

[11] Patent Number: 5,631,720
[45] Date of Patent: May 20, 1997

[54] OPHTHALMIC LENSES WITH HETEROCYCLIC CHROMENE COMPOUNDS

[75] Inventors: Robert Guglielmetti; Jean L. Pozzo; AndréSamat, all of Marseille, France

[73] Assignee: Essilor International (Compagnie Generale d'Optique), Echat, France

[21] Appl. No.: 625,727

[22] Filed: Mar. 29, 1996

Related U.S. Application Data

[63] Continuation of Ser. No. 33,893, Mar. 19, 1993, Pat. No. 5,527,911.

[30] Foreign Application Priority Data

Mar. 19, 1992 [FR] France ................... 93 03297

[51] Int. Cl.$^6$ ........................ G02C 7/10
[52] U.S. Cl. ......................... 351/163; 252/586
[58] Field of Search ............... 351/163; 359/642, 359/722; 252/586

[56] References Cited

U.S. PATENT DOCUMENTS

| | | | |
|---|---|---|---|
| 3,567,605 | 3/1971 | Becker | 204/157.09 |
| 4,556,605 | 12/1985 | Mogami et al. | 351/163 |
| 4,818,096 | 4/1989 | Heller et al. | 351/163 |
| 5,066,818 | 11/1991 | Gemert et al. | 549/389 |
| 5,266,447 | 11/1993 | Takahashi et al. | 430/345 |
| 5,274,132 | 12/1993 | Van Gemert | 351/163 |
| 5,349,065 | 9/1994 | Tanaka et al. | 546/15 |

FOREIGN PATENT DOCUMENTS

| | | |
|---|---|---|
| 0401958 | 12/1990 | European Pat. Off. |
| WO92/09593 | 6/1992 | WIPO |

OTHER PUBLICATIONS

Azerad, "No. 490.–Isomérisation acide des tocoquinones. II. – Synthèse de dichromannes apparentés aux tocoquinones," Bulletin de la Sociét''Chimique de France, 8:2728–2735, 1967, published in Europe (Month Unavailable).

Okazaki et al., "Preparation of Chromene Compounds as photochromic Substances," *Chemical Abstracts*, 115(19):1021, Abstract No. 207975k (No Date).

Tanaka et al., "Naphthopyrans and Analogs as Photochromic Agents and their Preparation," *Chemical Abstracts*, 113(9):Abstract No. 78167f, 1990, published in U.S.A. (Month Unavailable).

*Primary Examiner*—John A. McPherson
*Attorney, Agent, or Firm*—Arnold, White & Durkee

[57] ABSTRACT

The invention relates to ophthalmic lenses comprising a transparent organic polymer material and photochromic compounds of general formula

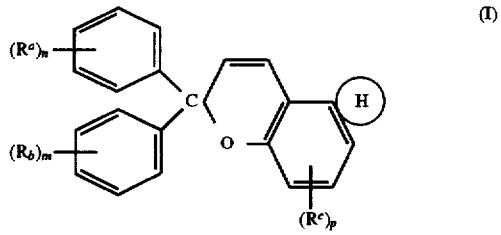

wherein $R^a$, $R^b$ and $R^c$ are hydrogen; alkyl; aryl; OR, SR, COR or COOR, where R denotes hydrogen, alkyl or aryl, amino of formula $NR_1R_2$ where $R_1$ and $R_2$ denote hydrogen, alkyl, cycloalkyl or an aryl; a halogen atom; a mono- or polyhaloalkyl group; or an $NO_2$, CN or SCN group; n and m denote integers from 1 to 5; p is equal to 1 or 2; and H is an aromatic heterocycle having the general formula:

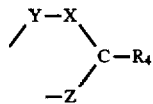

wherein:
X, Y and Z represent independently of each other, a $CR_8$ radical or a nitrogen atom, and one or two of X, Y and Z is a nitrogen atom and $R_8$ is selected from the group consisting of hydrogen, $C_1$–$C_6$ alkyl and phenyl; and $R_4$ is selected from the group consisting of hydrogen, $C_1$–$C_6$ alkyl and phenyl.

8 Claims, No Drawings

OPHTHALMIC LENSES WITH HETEROCYCLIC CHROMENE COMPOUNDS

The present application is a continuing application of U.S. patent application Ser. No. 08/033,893, filed Mar. 19, 1993, now U.S. Pat. No. 5,527,911.

The subject of the invention is novel photochromic compounds, more particularly, photochromic compounds containing in their chemical formula, a nucleus of the chromene or benzopyran family, and their use in the field of ophthalmic optics, in particular in and/or on ophthalmic lenses.

Photochromism is a phenomenon which has been known for many years. A compound is said to be photochromic when this compound changes color on irradiation with a light beam, some of whose wavelengths are situated in the ultraviolet region, and returns to its original color as soon as the irradiation ceases.

The applications of this phenomenon are numerous, but one of the known applications which is particularly advantageous, relates to the field of ophthalmic optics.

Such compounds can be used in the manufacture of spectacle lenses or glasses, for the purpose of screening out light radiation according to its intensity.

The incorporation of photochromic compounds in an organic material constituting an ophthalmic lens makes it possible to obtain a glass whose weight is greatly reduced compared with conventional lenses made from mineral glass, which contain silver halides by way of photochromic agent. Their incorporation in organic materials has always posed technical difficulties.

However, all compounds exhibiting photochromic properties are not necessarily usable in the field of ophthalmic optics. Indeed, the photochromic compound should meet a certain number of criteria, including among others:

- a high colorability which is a measure of the capacity of a photochromic compound to exhibit an intense color after isomerization;
- a coloration after absorption of light which makes the photochromic compound, alone or in combination with other photochromic compounds, capable of being used in ophthalmic glasses or lenses;
- an absence of coloration or very weak coloration in the initial form;
- a rapid coloration or decolorization kinetics;
- a photochromism which manifests itself within the widest possible temperature range, and in particular, preferably between 0° and 40° C.

The known organic photochromic compounds currently used generally exhibit a decreasing photochromism when the temperature increases, such that the photochromism is particularly pronounced at temperatures close to 0° C., whereas it is much fainter or even absent at temperatures of the order of 40° C. which are temperatures that can be achieved in glasses especially during exposure to sunlight.

Another problem encountered by the photochromic compounds of the state of the art is their lifetime. A relatively reduced lifetime is indeed observed for some products of the state of the art. Indeed, after a certain number of coloration and decolorization cycles, the photochromic compound generally gets stuck in an open and colored form and no longer exhibits reversible photochromic properties.

Many chromene type photochromic compounds have been synthesized by Professor HELLER in, for example, Patent Application EP 246,114 which describes a series of photochromic compounds in which a spiroadamantane group is introduced in position 2 of the benzopyran or naphthopyran nucleus, or even Patent Application WO 90/07507 where 2 cyclopropyl groups are attached in position 2 of the cyclic benzopyran or naphthopyran compound. Patent Application WO 91/00861 by the same inventor can also be mentioned, in which a norcamphor group or a tricyclodecane group is introduced in position 2 of photochromic compounds of the same type.

Benzopyran and naphthopyran type photochromic derivatives, substituted in position 2 of the pyran ring have already been described in U.S. Pat. No. 3,567,605. However, these compounds possess relatively low decolorization kinetic constants.

Moreover, photochromic derivatives also possessing low decolorization kinetic constants and less suitable for the application envisaged, are also known from Application EP-A-0,401,958.

The Applicant Company has discovered a novel family of benzopyrans possessing particularly advantageous photochromic properties. The compounds conforming to the invention indeed possess a high colorability, in particular in the red region, which is particularly useful in ophthalmic optics, it then being possible for these compounds to be used with photochromic compounds producing a blue color, so as to obtain a final natural coloration during exposure to light.

The compounds conforming to the invention possess, moreover, an absence of coloration or a very weak coloration in the initial state, and a rapid coloration and decolorization kinetics within a very wide temperature range, in particular between 0° and 40° C.

The Applicant also observed that these compounds possessed a particularly long lifetime.

The consequence of all these properties is that these novel photochromic compounds are particularly advantageous with respect to their use in ophthalmic optics and in particular to their use in and/or on ophthalmic lenses.

Within the context of the invention, ophthalmic lenses refer to spectacle glasses, in particular sunglasses and contact lenses.

One subject of the invention therefore consists of novel photochromic compounds.

Another subject of the invention consists of their use in ophthalmic optics.

The subject of the invention is also compositions intended to be used for coating ophthalmic lenses or their incorporation in these lenses.

Other subjects of the invention will emerge on reading the following description and examples.

The photochromic compound conforming to the invention is essentially of the general formula:

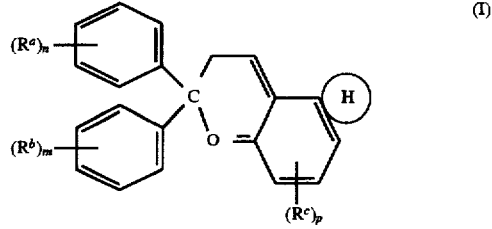

(I)

in which $R^a$, $R^b$ and $R^c$ denote, independently of each other, a hydrogen atom; an alkyl group; an aryl group; an OR, SR, COR or COOR group, in which R denotes a hydrogen atom, an alkyl group or an aryl group; an amino group of formula $NR_1R_2$ in which $R_1$ and $R_2$ denote, independently of each other, a hydrogen atom, an alkyl group, a cycloalkyl group, an aryl group, $R_1$ and $R_2$ being capable of forming with the nitrogen atom, a heterocycle containing 4 to 7 members and being capable of containing, in addition, one or more heteroatoms chosen from nitrogen, oxygen, sulfur, a halogen atom; a mono- or polyhaloalkyl group; an $NO_2$, CN or SCN group; n and m denote integers from 1 to 5 depending on the number of substitutions on the nucleus and p may be equal to 1 or 2 depending on the number of substitutions on the nucleus. The radicals $R^a$, $R^b$ and $R^c$ may have different meanings when m, n and p are greater than 1 and depending on the position on the nuclei; H is an aromatic heterocycle having 4 to 7 members and preferably 5 or 6 members containing one or more heteroatoms chosen from nitrogen, oxygen, sulfur, these heterocyclic nuclei being capable of being substituted by one or more alkyl, alkoxy, amino, aryl or aralkyl groups or condensed with an aromatic nucleus.

In the abovementioned formula, an alkyl group preferably denotes a group having 1 to 6 carbon atoms, a cycloalkyl group preferably denotes a group having 3 to 7 carbon atoms, the aryl group preferably denotes a phenyl group, halogen preferably denotes chlorine, bromine, fluorine, the polyhaloalkyl group preferably denotes a $CF_3$ group.

The heterocyclic nucleus is represented more particularly by the formula (II):

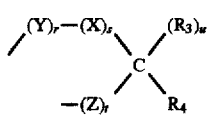

in which:

Y denotes $CR_5R_6$ in which $R_5$ and $R_6$ denote, independently of each other, hydrogen, $C_1$–$C_6$ alkyl, phenyl; $CR_5$, $R_5$ having the meaning given above, the carbon atom being linked to one of the neighboring atoms by a double bond; $NR_7$ in which $R_7$ denotes hydrogen, $C_1$–$C_6$ alkyl or N - linked to the neighboring atom by a double bond; oxygen or sulfur; r being equal to 0 or 1;

X and Z denote, independently of each other, $CR_8R_9$, in which $R_8$ and $R_9$ denote, independently of each other, hydrogen, $C_1$–$C_6$ alkyl, phenyl; $CR_8$–$R_8$ having the meaning given above and the carbon atom being linked to the neighboring atom by a double bond; $NR_{10}$ where $R_{10}$ denotes hydrogen or $C_1$–$C_6$ alkyl or alternatively N - linked to the neighboring atom by a double bond; oxygen, sulfur, s or t is equal to 0 or 1 and the sum r+s+t is not less than 2 and at least one of the groups Y, X, Z denotes NH—, —N—; —O— or —S, the meanings —N—, —O—, —S— being preferred;

$R_3$ and $R_4$ denote, independently of each other, hydrogen, $C_1$–$C_6$ alkyl, phenyl, u is equal to 0 or 1 and the carbon atom forming with one of the neighboring carbon atoms, a double bond when u is equal to 0, $R_3$ and X or $R_4$ and Z being capable of forming together elements of a ring having 5 or 6 members which are aromatic or non-aromatic, preferably benzene, or a naphthalene nucleus optionally substituted by a $(R_{11})_v$ group, $R_{11}$ having the meaning of any one of the groups $R^a$, $R^b$ and $R^c$, as defined above and v being an integer from 0 to 4 in the case of a benzene ring or from 0 to 6 in the case of a naphthalene ring.

The heterocyclic nuclei particularly preferred are chosen from the groups of formula (II), in which r is equal to 0, X denotes O, S or N, Z denotes $CR_8R_9$ or X denotes $CR_8R_9$ and Z denotes O, S or N and $R_3$, $R_4$, $R_5$, $R_8$, $R_9$ have the meanings given above, and when Z or alternatively X denotes $CR_8$, $R_4$ and $R_8$ or alternatively $R_3$ and $R_8$ may together form an optionally substituted benzene ring; X preferably denotes O or S.

Other preferred compounds are those for which r+s+t=3, and at least one of the groups X, Y or Z denotes N, at least one of these groups denoting $CR_8R_9$ or $CR_8$; Z preferably denotes N, X or Y denote N and the other $CR_8$, $R_8$, $R_9$ having the meanings given above.

The heterocyclic nuclei more particularly preferred are chosen from pyrimidine, pyrazine, furan nuclei, optionally condensed with an aromatic nucleus to form an optionally substituted benzofuran, thiazole ring.

The families of compounds more particularly preferred are of the formulae:

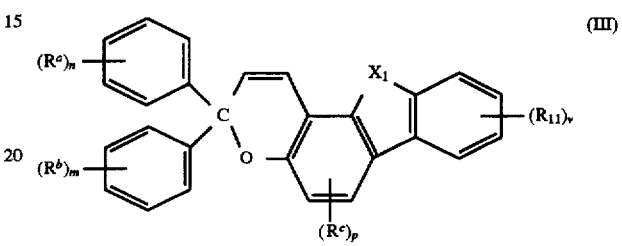

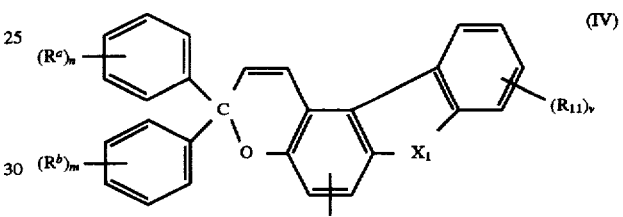

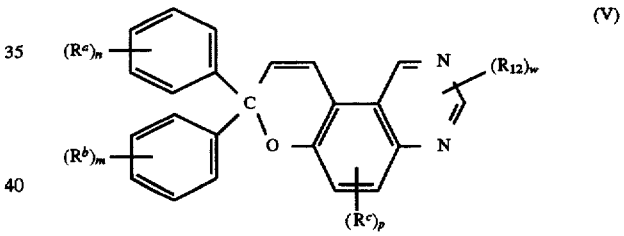

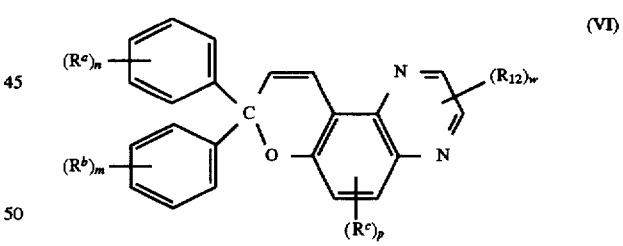

in which $R^a$, $R^b$, $R^c$, $R_{11}$ and n, m, p and v have the meanings given above, $X_1$ meaning oxygen or sulfur and preferably oxygen, $R_{12}$ having the meaning given for $R_{11}$ and w being an integer from 0 to 2.

The compounds conforming to the invention may be prepared according to the following reaction scheme:

REACTION SCHEME A

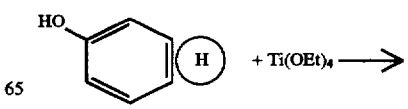

-continued
REACTION SCHEME A

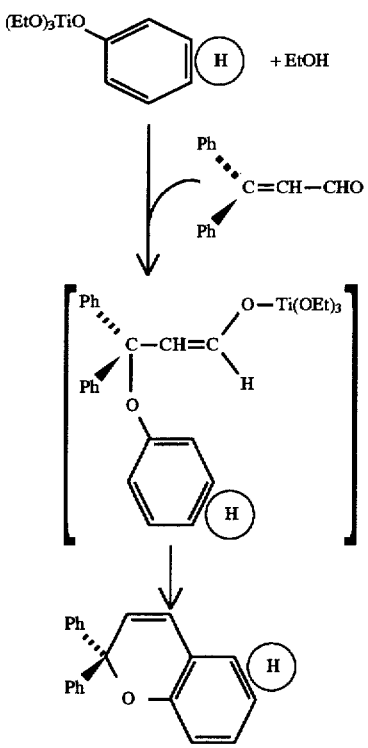

In these formulae, H denotes a heterocyclic group having the meaning given above. The phenyl groups may be substituted by a group $R^a$ or $R^b$ as defined above.

The photochromic compounds conforming to the invention may be used for producing photochromic ophthalmic lenses.

The compounds conforming to the invention may be introduced into a composition intended to be applied on or to be introduced into a transparent organic polymer material to give a transparent photochromic article. They may also be introduced into solid compositions such as plastic films, patches and lenses for producing materials which can be used especially as ophthalmic lenses, sunglasses, viewfinders, camera optics and screening agents.

The liquid compositions which constitute a subject of the invention essentially contain, in dissolved or dispersed form, the compounds conforming to the invention in a medium based on solvents suitable for applying to or introducing into a transparent polymer material.

Solvents which can be more particularly used are organic solvents chosen from benzene, toluene, chloroform, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methyl cellosolve, morpholine and ethylene glycol.

When the compounds conforming to the invention are dispersed, the medium may also contain water.

According to another embodiment, the compounds conforming to the invention may be introduced and preferably dissolved in colorless or transparent solutions prepared from polymers, copolymers or mixtures of polymers which are transparent in a suitable organic solvent.

Examples of such solutions are among others, solutions of nitrocellulose in acetonitrile, polyvinyl acetate in acetone, polyvinyl chloride in methyl ethyl ketone, polymethyl methacrylate in acetone, cellulose acetate in dimethylformamide, polyvinylpyrrolidone in acetonitrile, polystyrene in benzene, ethyl cellulose in methylene chloride.

These compositions may be applied on transparent supports such as in polyethylene glycol terephthalate, borylated paper, cellulose triacetate, and dried to give a photochromic material which can become colored in the presence of ultraviolet radiation and which returns to its noncolored and transparent state in the absence of the radiation source.

The photochromic compounds of the present invention or the above defined compositions containing them, may be applied or incorporated in a solid transparent polymerized organic material suitable for ophthalmic elements such as ophthalmic lenses or materials useful for use in sunglasses, viewfinders, camera optics and screening agents.

The following may be mentioned as transparent solid materials which may be used to produce ophthalmic lenses conforming to the invention: polyol(allyl carbonate), polyacrylate, poly(alkyl acrylate) polymers such as polymethyl methacrylates, cellulose acetate, cellulose triacetate, cellulose propionate acetate, cellulose butyrate acetate, poly (vinyl acetate), poly(vinyl alcohol), polyurethanes, polycarbonates, polyethylene terephthalates, polystyrenes, (polystyrene methyl methacrylates), styrene and acrylonitrile copolymers, polyvinyl butyrates.

Transparent copolymers or mixtures of transparent copolymers are also suitable for producing such materials.

In this respect, there may be mentioned materials prepared from polycarbonates such as poly[2,2-(4,4'-dioxydiphenol) propane], polymethyl methacrylate, polyol(allyl carbonate) such as in particular diethylene glycol bis(allyl carbonate) and its copolymers such as for example with vinyl acetate. There may be mentioned in particular the copolymers of diethylene glycol bis(allyl carbonate) and vinyl acetate (80–90/10–20) and even the copolymer of diethylene glycol bis(allyl carbonate) with vinyl acetate, cellulose acetate and cellulose propionate, cellulose butyrate (80–85/15–20).

The polyols(allyl carbonate) are prepared using allyl carbonates of linear or branched, aliphatic or aromatic liquid polyols such as the aliphatic glycols of bis(allyl carbonate) or alkylene bis(allyl carbonates). Among the polyol(allyl carbonates) which may be used for preparing the transparent solid materials which may be used in accordance with the invention, there may be mentioned ethylene glycol bis(allyl carbonate), diethylene glycol bis(2-methylallylcarbonate), diethylene glycol bis(allyl carbonate), ethylene glycol bis (2-chloroallylcarbonate), triethylene glycol bis(allyl carbonate), 1,3-propanediol bis(allyl carbonate), propylene glycol bis(2-ethylallylcarbonate), 1,3-butanediol bis(allyl carbonate), 1,4-butanediol bis(2-bromoallylcarbonate), dipropylene glycol bis(allyl carbonate), trimethylene glycol bis(2-ethylallylcarbonate), pentamethylene glycol bis(allyl carbonate), isopropylene bisphenol bis(allyl carbonate). The most important product consists of diethylene glycol bis (allyl carbonate) also known under the name CR39.

The amount of photochromic compounds to be used in conformity with the invention, either in the composition or at the time of its introduction into the solid support, is not critical and generally depends on the intensity of the color which the composition can confer on the material after exposure to radiation. Generally, the greater the amount of photochromic compounds added, the more intense the coloration will be under irradiation.

In conformity with the invention, a sufficient amount is used to confer on the treated material the property of changing color on exposure to radiation. This amount of photochromic compounds is generally between 0.01 and 20% by weight, and preferably between 0.05 and 10% by weight relative to the total weight of the optic material or composition.

The photochromic compounds conforming to the invention may also be introduced into a temporary transfer carrier (such as a varnish forming a coating on a substrate) and be subsequently thermally transferred in the substrate as described in particular in Patent U.S. Pat. No. 4,286,957 or U.S. Pat. No. 4,880,667.

These compounds may be used with other photochromic compounds such as photochromic compounds giving rise to various colorations such as blue and green, which are known in the state of the art. Accordingly, spiro-(indoline-oxazines), which are well known in the state of the art, may be used.

Once applied to the ophthalmic materials or introduced into such materials, the appearance of a coloration is observed after exposure to UV radiation, and there is a return to the original color or transparency when the exposure to UV radiation is discontinued.

The compounds conforming to the invention have the advantage of permitting this change in coloration many times and this at temperatures which vary widely between 0° and 40° C.

The following examples are intended to illustrate the invention without, however, being of a restrictive nature.

EXAMPLE 1

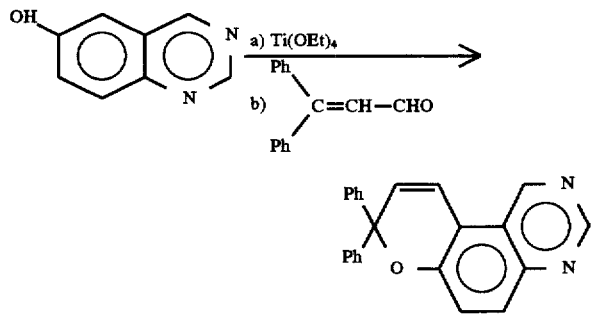

2.09 g of 6-hydroxyquinazoline ($1.43 \times 10^{-2}$ mole) are dissolved in 10 ml of anhydrous toluene and placed under an inert atmosphere.

A stoichiometric toluene solution of orthotitanate is added. The reaction mixture is then refluxed for 1 hour. The heating is then continued so as to remove the ethanol thus formed. After reequilibrating to room temperature, 1.46 g ($7.01 \times 10^{-3}$ mole) of β-phenylcinnamaldehyde are added. The reflux is then continued for 2 hours under an inert atmosphere. After reequilibrating to room temperature, the reaction mixture is extracted using a 2M solution of ammonium chloride and then extracted three times using a 2M solution of sodium hydroxide.

The mixture is dried over MgSO$_4$. The solvent is removed using a rotary evaporator. 50 ml of hexane are added. The precipitate is recovered and recrystallized from cyclohexane (white solid).

melting point=162° C.

Yield=43%.

When a toluene solution of the compound of Example 1 is irradiated with UV radiation, the solution becomes red (438 nm), when the ultraviolet radiation is stopped, the solution becomes colorless again.

EXAMPLE 2

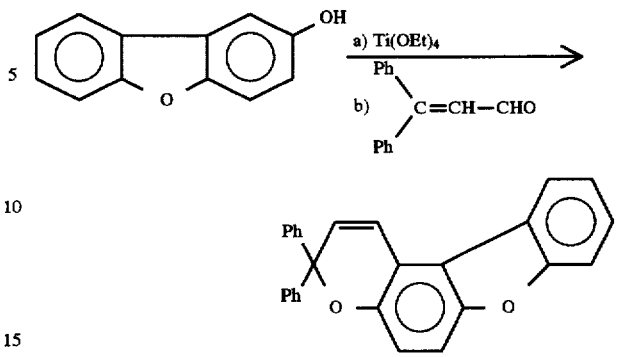

a) 2-Hydroxydibenzofuran (1.842 g, $10^{-2}$ mole) is dissolved in anhydrous toluene. A stoichiometric toluene solution of ortho-titanate is added. The reaction mixture is refluxed for 30 minutes and then the ethanol thus formed is distilled off.

b) After reequilibrating to room temperature, a toluene solution of β-phenylcinnamaldehyde (1.041 g, $5 \times 10^{-3}$ mole) is slowly added. The reflux is continued under an inert atmosphere for 1 h 30 minutes.

After reequilibrating to room temperature, the solvent is removed using a rotary evaporator. Dichloromethane and a 2N solution of sodium hydroxide are then added.

The mixture is extracted continuously for 24 hours. It is dried over MgSO$_4$. The solvent is removed using a rotary evaporator.

The chromene obtained is purified by flash chromatography (100% pentane). It is recrystallized from cyclohexane (yellow solid).

melting point=134° C.

Yield=40%.

When a toluene solution of Example 2 is irradiated with UV radiation, the solution becomes red (505 nm), when the ultraviolet radiation is stopped, the solution becomes colorless again.

EXAMPLE 3

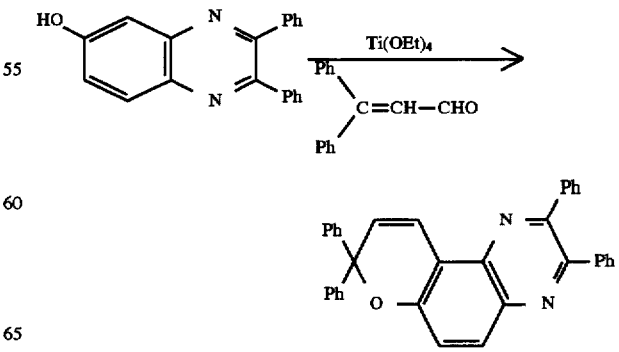

Stage 1: Synthesis of 6-hydroxy-2,3-diphenylquinoxaline a) 6-Methoxy-2,3-diphenylquinoxaline

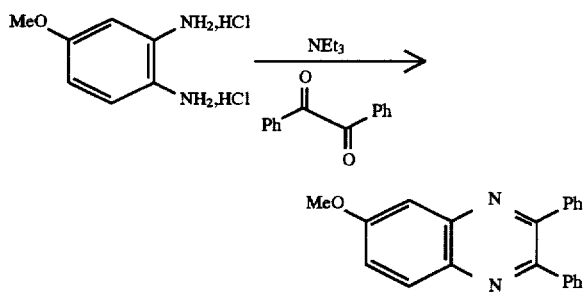

2 g of 4-methoxy-1,2-phenylenediamine dihydrochloride (1.15×10$^{-2}$ mole) are dissolved in 20 ml of anhydrous ethanol under an inert atmosphere.

A stoichiometric ethanolic solution of triethylamine is added. The stirring is continued at room temperature for 30 minutes. An ethanolic solution of benzil (2.46 g, 1.17×10$^{-2}$ mole) is added. The reaction mixture is refluxed for 4 hours. The precipitate formed is recovered by filtration. It is dried under vacuum to obtain 2.4 g of the desired compound.

melting point=152° C.
Yield=70%.

b) 6-Hydroxy-2,3-diphenylquinoxaline

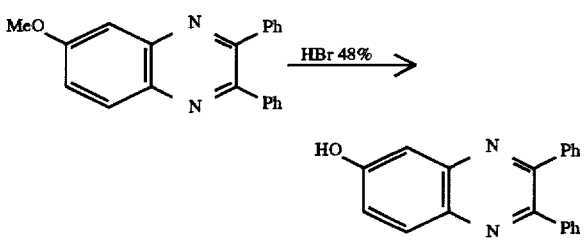

A mixture of 6-methoxy-2,3-diphenylquinoxaline (1 g; 3.2×10$^{-3}$ mole) and 10 ml of HBr (48%) is heated at 120° C. for 9 hours. After reequilibrating to room temperature, the solution is neutralized (pH:7.5) with a 1M solution of NH$_4$OH.

The precipitate formed is recovered by filtration and purified by flash chromatography (99% CHCl$_3$, 1% CH$_3$OH). The solvent is removed using a rotary evaporator.

melting point=251° C.
Yield=43%.

Stage 2 a) 6-Hydroxy-2,3-diphenylquinoxaline (1 g, 3.37×10$^{-3}$ mole) is dissolved in anhydrous toluene. A stoichiometric toluene solution of ortho-titanate is added. The reaction mixture is refluxed for 30 minutes and then the ethanol thus formed is distilled off.

b) After reequilibrating to room temperature, a toluene solution of β-phenylcinnamaldehyde (0.33 g, 1.58×10$^{-3}$ mole) is slowly added. The mixture is refluxed under an inert atmosphere for 2 hours.

After reequilibrating to room temperature, the reaction mixture is extracted with a 2M solution of ammonium chloride, and then three times with a 2M solution of sodium hydroxide. It is dried over MgSO$_4$. The solvent is removed using a rotary evaporator. 25 ml of cyclohexane are added. A precipitate is recovered and purified by chromatography (100% ether). It is recrystallized from cyclohexane (white solid).

melting point=159° C.

Yield=10%

EXAMPLE 4

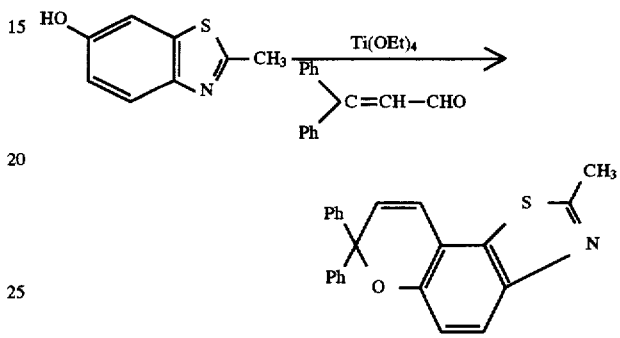

Stage 1: Synthesis of 6-hydroxy-2-methylbenzothiazole 1 g of commercial 6-methoxy-2-methylbenzothiazole (5.5×10$^{-3}$ mole) is mixed with 0.9 g of azeotropic hydrobromic acid at 48% (1.1×10$^{-2}$ mole). The reaction is carried out in a sealed tube at 125° C. for 6 hours.

After neutralizing the solution with 3N ammonium hydroxide (pH=7), the hydroxylated compound is extracted with chloroform. The yield is quantitative. (Synthesis described in French Patent FR-2,647,790).

melting point=147° C.

Stage 2

0.965 g of 6-hydroxy-2-methylbenzothiazole (5.83×10$^{-3}$ mole) is dissolved in 10 ml of anhydrous toluene and placed under an inert atmosphere.

A stoichiometric toluene solution of orthotitanate is added. The reaction mixture is then refluxed for 30 minutes. The heating is then continued so as to remove the ethanol thus formed. After reequilibrating to room temperature, 0.585 g (2.8×10$^{-3}$ mole) of β-phenylcinnamaldehyde is added. The reflux is continued for 1 h 30 minutes under an inert atmosphere. After reequilibrating to room temperature, the reaction mixture is extracted with a 2M solution of ammonium chloride, and then three times with a 2M solution of sodium hydroxide.

The mixture is dried over MgSO₄. The solvent is removed using a rotary evaporator. 50 ml of hexane are added. The precipitate is recovered and recrystallized from cyclohexane (yellow solid).

melting point=215° C. Yield=35%

TABLE 1

Spectrokinetic parameters in toluene at 25° C., at a concentration of $2.5 \times 10^{-5}$ M

| Examples | Color of photo-merocyanine | $\lambda_{max}$ (nm) | Kinetic constant of thermal decolorization K in $s^{-1}$ | $A_o$ (color-ability) |
|---|---|---|---|---|
| 1 | Red | 438 | 0.47 | 1.03 |
| 2 | Red | 505 | 0.23 | 0.41 |
| 3 | Red | 471 | 0.1 | 0.93 |
| 4 | Red | 430–508 | 0.25 | 0.14 |

EXAMPLE 5

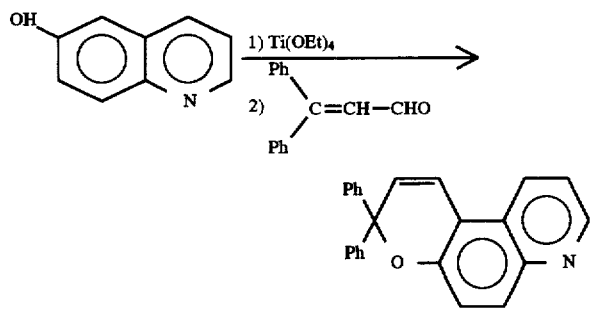

a) 3 g of 6-quinolinol ($2.07 \times 10^{-2}$ mole) are dissolved in anhydrous toluene. A stoichiometric solution of orthotitanate (4.722 g, equivalent to $2.07 \times 10^{-2}$ mole of orthotitanate) is added. The mixture is refluxed for 1 hour and then the ethanol formed is distilled off.

b) a toluene solution of β-phenylcinnamaldehyde (2.047 g, $9.83 \times 10^{-3}$ mole) is then slowly added.

After reequilibrating to room temperature, the mixture is washed with a solution of ammonium chloride, and then with a 2M solution of sodium hydroxide.

The aqueous phase is dried over MgSO₄ and the solvent is removed under reduced pressure.

The product is purified by flash chromatography (80% pentane, 20% Et₂O). It is recrystallized from a xylene-heptane mixture.

Melting point=222° C.

Yield=62%.

EXAMPLE 6

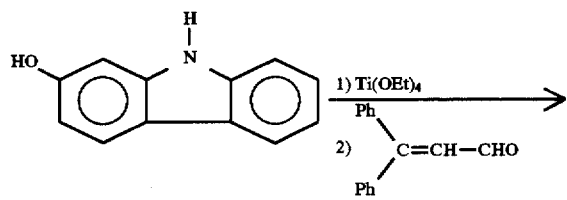

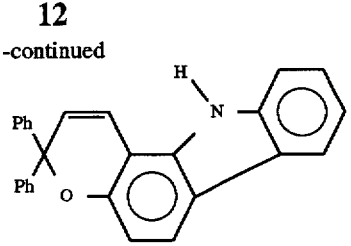

1.832 g (10 mmol) of 2-hydroxycarbazole are dissolved in 50 ml of anhydrous toluene and placed under an inert atmosphere.

A toluene solution (10 ml) of 2.28 g of orthotitanate (10 mmol) is gradually added.

The reaction mixture is heated at the reflux temperature of toluene for 40 minutes and the ethanol is simultaneously distilled off.

The mixture is allowed to reequilibriate to room temperature before adding a toluene solution (35 ml) of 1 g of β-phenylcinnamaldehyde (4.8 mmol). When the addition is complete, the mixture is refluxed for 2 hours. The solvent is removed under reduced pressure.

The product is rinsed with a 2M solution of NH₄Cl and then with a 2M solution of NaOH. A large quantity of emulsion then appears which is taken up in chloroform. The solution is allowed to settle.

The aqueous phase is filtered after adjusting the pH to 8.5. The alcohol is recovered.

The solvent of the organic phase is removed under reduced pressure. The residue precipitates from hexane. It is filtered. The product obtained is purified by flash chromatography, using a pentane/ether mixture (75/25) as eluent.

Mass obtained=0.3 g

Molecular weight (g. mol.)=375.5

Melting point=182° C.

Yield=17%

TABLE 2

Spectrokinetic parameters in toluene at 25° C., at a concentration of $2.5 \times 10^{-5}$ M

| Examples | Color of photo-merocyanine | $\lambda_{max}$ (nm) | Kinetic constant of thermal decolorization K in $s^{-1}$ | $A_o$ (color-ability) |
|---|---|---|---|---|
| 5 | Orange | 436 | 0.13 | 0.61 |
| 6 | Red | 436 | 0.15 | 0.99 |

EXAMPLE 7

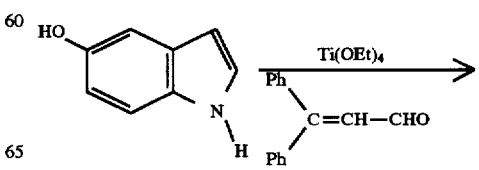

13

-continued

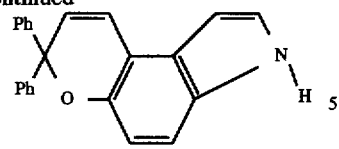

0.77 g of 5-hydroxyindole (5.77×10⁻³ mole) is dissolved in 10 ml of anhydrous toluene and placed under an inert atmosphere.

A stoichiometric toluene solution of orthotitanate is added. The reaction mixture is then refluxed for 40 minutes. The heating is then continued so as to remove the ethanol thus formed. After reequilibrating to room temperature, 0.55 g (2.66×10⁻³ mole) of β-phenylcinnamaldehyde is added. The reflux is then continued for 1 hour 30 minutes under an inert atmosphere. After reequilibrating to room temperature, the reaction mixture is extracted with a 2M solution of ammoniumchloride, and then three times with a 2M solution of sodium hydroxide.

The mixture is dried over MgSO₄. The solvent is removed using a rotary evaporator. It is purified by chromatography on silica (100% toluene). A red oil is recovered and crystallized from pentane.

melting point=143° C.
Yield=33%.

EXAMPLE 8

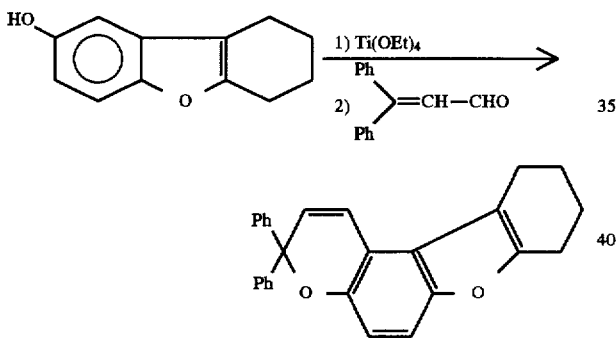

2.16 g (1.146×10⁻² mole) of 2-hydroxy-5,6,7,8-tetrahydrodibenzofuran are dissolved in 10 cm³ of toluene, and then a stoichiometric solution of ortho-titanate (2.614 g, 1.146×10⁻² mole) is added.

The mixture is refluxed for 1 hour and then the ethanol formed is distilled off.

The mixture is reequilibriated to room temperature.

A toluene solution containing 1.313 g, equivalent to 6.3×10⁻³ mole of β-phenylcinnamaldehyde, is then added.

The mixture is refluxed for 3 h 30 minutes.

After reequilibriating to room temperature, the reaction medium is extracted with 2M sodium hydroxide.

The mixture is dried over MgSO₄ and the solvent is removed.

The product is purified by flash chromatography (85% hexane, 19% Et₂O). It is recrystallised from a benzene-heptane mixture.

Melting point=187° C.
Yield=10%.

We claim:

14

1. An ophthalmic lens comprising a transparent organic polymer material and at least one photochromic compound which is of the original formula:

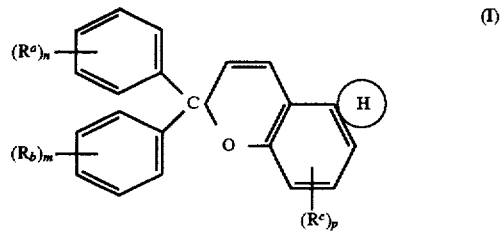

(I)

wherein $R^a$, $R^b$ and $R^c$ denote, independently of each other, a hydrogen atom, an alkyl group, an aryl group, an OR, SR, COR or COOR group, where R denotes a hydrogen atom, an alkyl group or an aryl group, an amino group of formula $NR_1R^2$ where $R^1$ and $R^2$ denote, independently of each other, a hydrogen atom, an alkyl group, a cycloalkyl group or an aryl group; a halogen atom; a mono- or polyhaloalkyl group; or an $NO_2$, CN or SCN group; n and m denote integers from 1 to 5; p is equal to 1 or 2; $R^a$, $R^b$ and $R^c$ may have different meanings when m, n and p are greater than 1; and H is an aromatic heterocycle having the general formula:

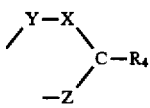

wherein:

X, Y and Z represent independently of each other, a $CR_8$ radical or a nitrogen atom, and one or two of X, Y and Z is a nitrogen atom and $R_8$ is selected from the group consisting of hydrogen, $C_1$–$C_6$ alkyl and phenyl; and $R_4$ is selected from the group consisting of hydrogen, $C_1$–$C_6$ alkyl and phenyl, said at least one photochromic compound being present in a sufficient amount to enable the ophthalmic lens to change color upon exposure to ultraviolet radiation.

2. The ophthalmic lens of claim 1, wherein the photochromic compounds comprise compounds of a formula:

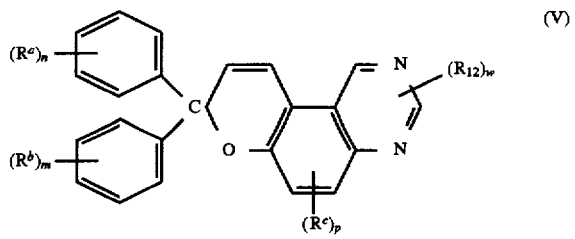

(V)

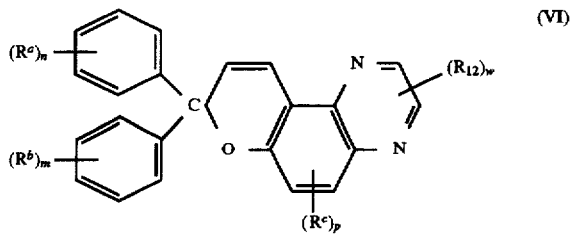

(VI)

wherein $R^a$, $R^b$, $R^c$, n, m and p have the meanings given in claim 1, $R_{12}$ has the meaning given for $R_8$; and w is an integer from 0 to 2.

3. The ophthalmic lens of claim 1 comprising compounds of a formula:

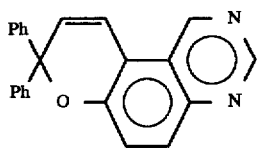

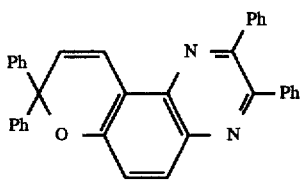

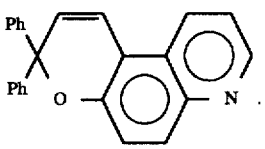

4. The ophthalmic lens of claim 1 wherein said at least one photochromic compound is in the form of a coating on said transparent organic polymer material.

5. The ophthalmic lens of claim 1 wherein the amount of photochromic compounds ranges from 0.01 to 20% by weight relative to the total weight of the transparent organic polymer material and photochromic compounds.

6. The ophthalmic lens of claim 5, wherein the amount of photochromic compounds ranges from 0.05 to 10% by weight relative to the total weight of the transparent organic polymer material and photochromic compounds.

7. The ophthalmic lens of claim 1, wherein said transparent organic polymer material is selected from the group consisting of polyol(allylcarbonate), polyacrylate, poly(alkylacrylate) polymers, cellulose acetate, cellulose triacetate, cellulose propionate acetate, cellulose butyrate acetate, poly(vinylacetate), poly(vinyl alcohol), polyurethanes, polycarbonates, poly(ethylene terephthalates), polystyrenes, poly(styrene methylmethacrylates), styrene and acrylonitrile copolymers, and polyvinylbutyrates.

8. The ophthalmic lens of claim 1, wherein said transparent organic polymer material is selected from the group consisting of poly[2,2-(4,4'-dioxydiphenol) propane], poly(methylmethacrylate) and polyol(allylcarbonates).

* * * * *

UNITED STATES PATENT AND TRADEMARK OFFICE
CERTIFICATE OF CORRECTION

PATENT NO.   :   5,631,720
DATED        :   May 20, 1997
INVENTOR(S)  :   Guglielmetti et al.

It is certified that error appears in the above-identified patent and that said Letters Patent is hereby corrected as shown below:

In claim 1, column 14, line 18, delete "$R^2$ where $R^1$ and $R^2$" and insert therefor --$R_2$ where $R_1$ and $R_2$--.

Signed and Sealed this

Twenty-ninth Day of July, 1997

Attest:

BRUCE LEHMAN

*Attesting Officer*      *Commissioner of Patents and Trademarks*